United States Patent [19]
DuBrock, Jr. et al.

[11] Patent Number: 5,205,177
[45] Date of Patent: Apr. 27, 1993

[54] METHOD AND APPARATUS FOR GAS MONITORING

[75] Inventors: Robert E. DuBrock, Jr., Dana Point; Donald J. Kohout, Lake Elsinore, both of Calif.

[73] Assignee: Research-Cottrell, Inc., Somerville, N.J.

[21] Appl. No.: 644,706

[22] Filed: Jan. 23, 1991

[51] Int. Cl.⁵ .............................................. G01N 1/14
[52] U.S. Cl. ............................................. 73/863.12
[58] Field of Search ............ 73/863.12, 863.81, 863.83, 73/864.81

[56] References Cited

U.S. PATENT DOCUMENTS

| | | | |
|---|---|---|---|
| 3,581,473 | 6/1971 | Ririe, Jr. et al. | 73/863.12 |
| 3,593,023 | 7/1971 | Dodson et al. | 73/863.12 |
| 4,147,500 | 4/1979 | Karlsoen | 73/863.12 |
| 4,191,541 | 3/1980 | Jenkins | 73/863.12 |
| 4,304,102 | 12/1981 | Gray | 62/475 |
| 4,317,379 | 3/1982 | Oberlander et al. | 73/863.83 |
| 4,336,722 | 6/1982 | Schweitzer | 73/863.12 |
| 4,578,986 | 4/1986 | Navarre | 73/863.83 |
| 4,883,505 | 11/1989 | Lucero | 73/864.81 |
| 4,942,722 | 7/1990 | Welker | 73/863.83 |

Primary Examiner—Robert Raevis
Attorney, Agent, or Firm—Howrey & Simon

[57] ABSTRACT

A method and apparatus for monitoring a flue gas is provided. The gas sampling system includes a conditioning unit proximate to a point where the sample is taken, an analyzing unit at a location removed from the point where the sample is taken and a gas sample transport line connecting the conditioning unit and analyzing unit.

1 Claim, 2 Drawing Sheets

METHOD AND APPARATUS FOR GAS MONITORING

BACKGROUND OF THE INVENTION

The invention relates to a monitoring system for sampling and analyzing gas in a gas stream. The invention more particularly relates to a system for continuously monitoring the gaseous components of a gas stream wherein analysis of the gas is conducted at a convenient location that may be remote from the point where the gas sample is taken.

In many processes, it is desirable to regularly analyze the products of combustion or the products of other reactions to determine the efficiency of the reaction and to monitor what effluents are being exhausted from the reactions. Government regulations often require periodic or continuous monitoring of gases exhausted from manufacturing or combustion processes. Monitoring and analyzing exhaust gases is complicated by the requirement that samples of the exhaust gas often must be taken from flue stacks shortly before the exhaust gas is expelled to the atmosphere. On the other hand, gas analysis is generally most conveniently conducted in an enclosed, climate-controlled structure on the ground. The distance between sample taking and analysis is especially troublesome when stack gases must be monitored near the outlet of a flue gas stacks that are hundreds of feet tall.

The distance between gas sampling locations and gas analysis locations has resulted in a variety prior art gas monitoring systems. In early monitoring systems, gas analysis equipment was housed at a convenient location on the ground and samples were periodically taken from a probe in the flue gas stack and physically carried to the analysis site. However, transporting samples is inconvenient and often dangerous. In addition, it is desirable in many processes to continuously monitor the components of a gas stream. Indeed, certain government regulations require continuous monitoring of exhaust gas streams.

In order to achieve continuous and convenient gas monitoring, stack sample probes have been connected to gas analysis equipment through long sample lines. In such systems, a pump near the gas analysis equipment creates a suction in the long sample line that pulls gas into the sample probe and down the sample line to the pump whose outlet discharges sampled gas to the gas analysis equipment. Continuous monitoring systems with long sample transport lines introduce a number of gas monitoring inaccuracies. For example, when a heated gas sample taken from the flue stack is carried the length of a long sample transport line, the sample cools and liquid vapor in the sample condenses in the sample transport line. This condensed liquid gathers on the walls of the transport line and collects at low points along the transport line. When a liquid condensate forms in the sample transport line, the condensed liquids absorb contaminants passing through the gas line. The absorbed gas contaminants will not be detected by the analysis equipment at the time the gas contaminants are sampled. In addition, the condensate may later emit the absorbed gases or the condensate may react with a later gas sample resulting in additional inaccuracies. Thus, once liquid forms in the sample transport line, accurate gas monitoring becomes impossible.

To overcome the problem of condensation formation in the gas transport line, prior art systems insulated and heated the sample transport line such that the sample gas was kept heated between the sampling point and the gas analyzer. This heating was designed to prevent condensation in the transport line. However, gas transport line heaters periodically break down. After such breakdowns are discovered, it is necessary to turn off the monitoring system and clean condensate out the gas transport line. This maintenance is both expensive and time consuming.

One approach to overcoming the problems associated with long sample transport lines has been to move the gas analyzer to a location close to the gas sampling probe. In such systems, the gas analyzer is mounted on the flue gas stack near the sample probe and the analysis results are transmitted over electrical wires to a convenient location where the results are printed out on a terminal. Unfortunately, many gas analyzers are too large or too sensitive to be mounted on a flue gas stack and regular maintenance and calibration of gas analyzers is made inconvenient by locating analyzers on the flue gas stack.

Another problem associated with long sample transport lines in prior art monitoring systems is that the gas samples are pulled from the sample probe to the analyzer under suction. If there are any leaks in the long sample transport line, this suction pulls contaminants into the sample.

SUMMARY OF THE INVENTION

Accordingly, it is an object of the invention to provide a gas monitoring system in which water vapor does not condense in a gas sample line between a stack mounted probe and a conveniently located gas sample analyzer.

It is another object of the invention to provide a system for reliably removing liquid vapor from a gas sample at a location close to where the gas sample is taken such that the gas sample may then be transported through an unheated gas sample transport line without condensation.

It is a further object of the invention to provide a mechanism for pumping a gas sample through a gas transport line under pressure such that leaks in the gas transport line do not result in the introduction of additional contaminants into the gas sample prior to gas sample analysis.

Additional objects and advantages of the present invention will be set forth in part in the description that follows and in part will be obvious from the description or may be learned by practice of the invention. The objects and advantages of the invention may be realized and obtained by the method and apparatus particularly pointed out in the appended claims.

To achieve the objects and in accordance with the purpose of the invention, as embodied and as broadly described herein, a system for sampling an exhaust gas and for analyzing the exhaust gas is provided. The system comprises a sampling means for sampling the exhaust gas and for providing an exhaust gas sample; conditioning means proximate the sampling means for receiving the gas sample and for removing moisture from the sample; analyzing means for analyzing the gas sample to determine the concentration of at least one gaseous component of the sample, the analyzing means being at a location removed from the sampling means and conditioning means; and a first gas sample transport line connecting the conditioning means and analyzing means, the first gas sample transport line being a conduit through which the gas sample is carried from the conditioning means to the analyzing means.

The accompanying drawings, which are incorporated in and constitute a part of this specification, illustrate presently preferred embodiments of the invention and, together with a description, serve to explain the principles of the invention.

DESCRIPTION OF THE PREFERRED EMBODIMENTS

Figure 1:
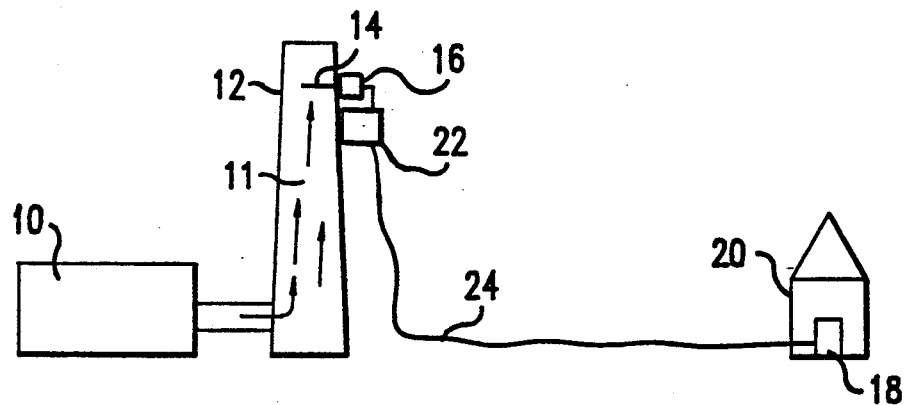
FIG. 1 is a diagrammatic illustration of a combustion plant to which the gas sampling and analyzing system of the present invention is applied.

Reference will now be made in detail to presently preferred embodiments of the invention, examples of which are illustrated in the accompanying drawings. Throughout the drawings, like reference characters are used to designate like elements.

Figure 2:
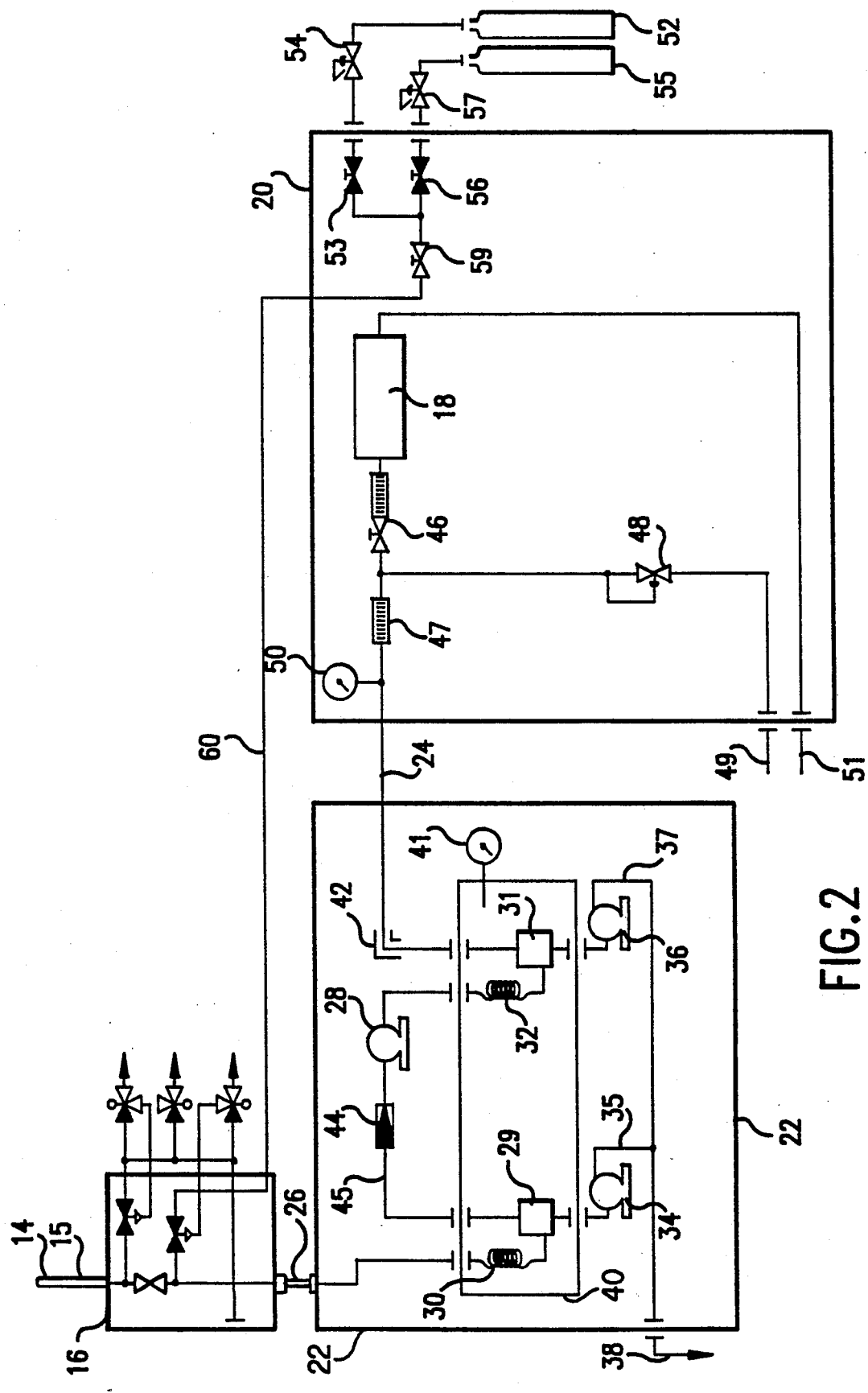
FIG. 2 is a schematic representation of the gas sampling and analyzing system of present invention.

A system for sampling an exhaust gas stream and for analyzing the gas stream sample is shown in FIGS. 1 and 2. FIG. 1 is a diagram showing a combustion unit 10 emitting an exhaust gas 11 through a flue stack 12. Combustion unit 10 could alternatively be any reaction vessel that emits an exhaust gas. The gaseous components of the exhaust gas are monitored by a monitoring system that includes a gas sample probe 14 a gas analyzer 18 and a gas conditioning unit 22.

According to the present invention, a system for sampling and analyzing a gas stream sample is provided. The system of the invention comprises sampling means for taking a gas sample from the gas stream; conditioning means proximate the sampling means for receiving the gas sample and for removing moisture from the gas sample; analyzing means for analyzing the gas sample to determine the concentration of at least one component of the gas sample, the analyzing means being at a location removed from the sampling means and conditioning means; and a first gas sample transport line connecting the conditioning means and analyzing means, the first gas sample transport line being a conduit through which the gas is carried from the conditioning means to the analyzing means. As embodied herein, a gas sample probe 14 is mounted on flue stack 12 to take samples of exhaust gas 11 being emitted through flue stack 12. Probe 14 is preferably a one half inch diameter pipe with a porous metal filter tip, as for example, a 3 micron sintered metal filter manufactured by Pall Porous Metals Filter Corporation of Courtland, New York. Sample probe 14 is connected to a gas conditioning unit 22 through a valve box 16. Gas conditioning unit 22 removes liquid vapor from the gas sample before the gas sample is transported to gas analyzer 18 through gas transport line 24. Gas conditioning unit 22 is located in close proximity with sample probe 14 such that a gas sample taken by the sample probe has to travel only a very short distance before liquid vapor is removed from the gas sample by conditioning unit 22. Once liquid vapor is removed from a gas sample, the gas sample can travel to a gas analyzer located at a convenient site some distance from the gas sample probe. Because gas conditioning unit 22 removes liquid vapor from the gas sample, liquid does not condense in gas transport line 24 so as to introduce inaccuracies into gas monitoring process.

FIG. 2 is a schematic drawing showing the system for sampling a gas stream and for analyzing the gas stream sample of the present invention. The basic elements of the system are sample probe 14, valve box 16, gas conditioning unit 22, and gas analyzer enclosure 20. These elements will be described in greater detail below. Valve box 16 is connected to gas conditioning unit 22 by a connector tube 26. Valve box 16 and connector tube 26 are preferably heated to a temperature sufficient to prevent condensation of liquid vapor in the gas sample before the gas sample reaches conditioning unit 22. Conditioning unit 22 is connected to gas analyzer housing 20 by gas transport line 24. Connector tube 26 and gas transport line 24 are preferably comprised of Teflon ® material. Connector tube 26 is heated and insulated such that gas passing through tube 26 is kept above the moister dew point of the gas (approximately 250° F.). Gas transport line 24 is preferably lightly insulated such that gas passing through line 24 does not fall below the freezing temperatures of any residual moisture in the gas (approximately 36° F.).

Gas conditioning unit 22 is mounted close to sample probe 14 and gas analyzer 18 is located at convenient location remote from the sampling position. Accordingly, connector tube 26 is very short while gas transport line 24 is many times longer than tube 26. For example, transport tube 26 is preferably 5 to 15 feet long while gas transport line 24 will often be hundreds of feet long. In some circumstances, gas conditioning unit 22 will be mounted hundreds of feet above the ground on a flue gas stack near a sample probe. In such circumstances, gas transport line 24 must be hundreds of feet long just to reach the ground and may be significantly longer to reach a convenient location for gas analyses.

As shown in FIG. 2, gas conditioning unit 22 preferably includes a gas sample pump 28 and gas cooling chambers housed within a refrigeration unit 40. A first cooling chamber comprises a first cooling coil 30, a first drain chamber 29, a first drain pump 34, and a first drain line 35. Similarly, a second cooling chamber comprises a second cooling coil 32, a second drain chamber 31, a second drain pump 36 and a second drain line 37. A sample pump 28 may be any low volume electric suction pump, as for example, ADI, DIA-VAC, diaphragm type sample pumps manufactured by Air Dimensions, Inc. of Lansdale, Penn. Drain pumps 34 and 36 are preferably low volume liquid suction pumps, as for example, MasterFlex peristaltic pumps manufactured by Cole Palmer Instrument Co. of Chicago, Ill.

When gas sample pump 28 of conditioning unit 22 is operated, sample pump 28 creates a suction in line 45 that pulls a sample into probe 14, through the valve box 16, through connecting tube 26, into cooling coil 30, through an inline filter 44, and then into the inlet of sample pump 28. When sample gas enters cooling coil 30, the gas cools due to the reduced temperature of refrigeration chamber 40, as monitored by temperature gauge 41. Refrigeration chamber 40 may hold a refrigerated gas or liquid that contacts cooling coils 30 and 32 to cool gas passing through the coils. When gas is cooled in cooling coil 30, liquid vapor in the gas sample condenses and collects in first drain chamber 29. The condensed liquid is withdrawn from first drain chamber 29 by first drain pump 34 that is a suction pump with an outlet connected to first drain line 34 which runs to main drain line 38.

Suction pump 28 draws the gas sample into the suction pump inlet and then discharges the gas sample under pressure out through the suction pump outlet. The sample gas exhausted out the pump outlet is forced under pressure through second cooling coil 32 and second drain chamber 31 of the second cooling chamber. Most of the liquid vapor remaining in the gas sample after the first cooling chamber is removed from the gas sample when the gas passes through second cooling coil 32. Liquid that condenses in second cooling coil 32 collects in second drain chamber 31 from which it is removed by second drain pump 36. Second drain pump 36 is preferably a suction pump whose outlet is connected to second drain line 37 that runs to a main drain line 38. Main drain line 38 may be connected into another drain line or may discharge into the open if only water vapor is being removed by conditioning unit 22.

After the gas sample passes through second drain chamber 31, the sample goes through a conductivity sensor 42 before exiting conditioning unit 22. Conductivity sensor 42 senses gas vapor content, and is preferably a conductivity sensor manufactured by Great Lakes Instruments, Inc. of Milwaukee, Wis. Conductivity sensor 42 may be connected to an alarm or other signal so as to signal a system operator whenever the liquid vapor level rises high enough such that condensation is possible in gas transport line 24. In the preferred embodiment of the invention, conductivity sensor 42 is electrically connected to gas sample pump 28 so as to immediately turn off gas sample pump 28 whenever the liquid vapor level exiting conditioning unit 22 rises above an acceptable limit.

Conditioning unit 22 yields excellent vapor removal because the gas sample passes through a condensing coil when the gas sample is at a pressure below ambient air pressure and through a second condensing coil when the gas sample is at a pressure above ambient air pressure. With this arrangement, sufficient liquid vapor is removed from the gas sample such that the gas may pass through a long unheated gas transport line 24, provided that the insulation on gas transport line 24 keeps the temperature in line 24 a few degrees above freezing (approximately 36° F.). In addition, because gas sample pump 28 pumps the sample gas through transport line 24 under a slight pressure, any small leaks in transport line 24 result in leakage of gas sample to the outside rather than the introduction of outside contaminants into gas sample transport line 24. There is no need to heat gas transport sample line 24 above the moisture dew point of the gas (approximately 250° C.) to prevent condensation of liquid vapor because gas conditioning unit 22 removes a sufficient amount of liquid vapor to prevent such condensation. However, in the event that the outside ambient temperature is so low that the insulation on gas transport line 26 does not keep gas in the line a few degrees above freezing, some heating of line 26 may be required to prevent residual moisture from forming ice plugs.

When gas transport line 24 enters analyzer housing 20, the sample gas is fed to either gas analyzer 18 or vented through gas sample vent 49. A rotometer valve 46 measures the gas volume entering gas analyzer enclosure 20 through gas transport line 24. A pressure regulator 48 holds a small back pressure on gas transport line 24 that is sufficient to prevent entry of contaminants into gas transport line 24 through small line leaks. Back pressure is monitored by pressure gauge 50. Valve 46 may be opened or closed to regulate the amount of gas sample supplied to gas analyzer 18. When valve 46 is opened, a gas sample passes through gas analyzer 18 before being vented to the atmosphere through vent 51. Analyzer 18 may be connected to a visual monitor or a printer to provide a read out reflecting the gaseous components of the gas sample Gas analyzer 18 may be any analyzer based on dry gas measurement, as for example an Ametek/Thermox WDGIII Oxygen Analyzer manufactured by Ametek of Pittsburgh, Penn. Gas analyzer housing 20 is climate controlled because most gas analyzers operate best at room temperature without exposure to the elements.

According to the embodiment of the invention shown in FIG. 2, gas analyzer housing 20 also includes valves for regulating the introduction of a calibration gas into the gas analyzer. One or more calibration gases may be used, depending upon the gaseous components being monitored by gas analyzer 18. As shown in FIG. 2, calibration gas canisters 52 and 55 are connected to a calibration gas line 60 through valve and regulator combinations 53, 54, and 56, 57, respectively. Gas line 60 is preferably a 1/2 inch line comprised of a Teflon® material. Valves 53 and 56 are preferably solenoid valves. When it is desired to calibrate gas analyzer 18, one of the valves 53 or 56 is opened and trim valve 59 is opened such that the calibration gas enters calibration gas line 60 at a pressure equal to the gas pressure when in normal sampling mode.

Figure 3:
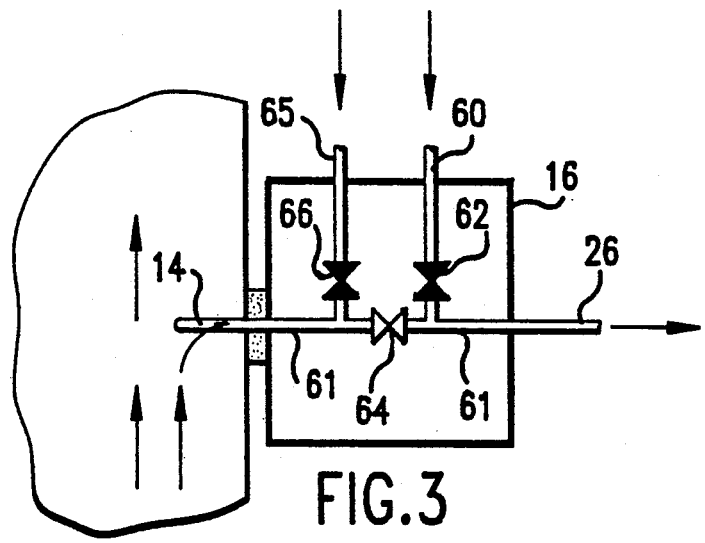
FIG. 3 is a enlarged view of the valve box and sampling probe of the gas sampling and analyzing system shown in FIG. 2.

Calibration line 60 follows the path of gas transport line 24 back to the valve box 16 where calibration line 16 connects to the gas sample line and valve box 16. As shown in FIG. 3, calibration line 60 enters valve box 16 to connect with sample line 61 through calibration line valve 62. In the preferred embodiment of the invention, a pressurized air line 65 also enters valve box 16 to connect with sample line 61 through a pressurized air line valve 66. A sample line valve 64 is positioned on sample line 61 between the junction of the calibration line 60 and sample line 61 and the junction of the pressurized air line 65 and sample line 61. Preferably, valves 62, 64 and 66 are ball valves, as for example Whitey SS-62TF4-31C manufactured by Whitey Company of Highland Heights, Ohio. Valves 62, 64 and 66 may be solenoid valves that are capable of being electronically opened and closed by an operator stationed in the gas analyzer enclosure 22.

When it is desired to analyze a gas sample 11 from stack 12, valve 64 is opened while valves 66 and 62 are closed and gas sample pump 28 is turned on. Alternatively, when it is desired to calibrate gas analyzer 18, valve 62 is opened while valve 64 is closed after which gas sample pump 28 is turned on such that calibration gas 60 is drawn to the sample pump 28 and then pumped to gas analyzer 18. By introducing a calibration gas into valve box 16 on which the sample probe 14 is mounted, any system leaks between valve box 16 and gas analyzer 18 will be detected during calibration. Alternatively, when it is desired to clean particulates out of sample probe 14, valve 66 is opened while valve 64 is closed. Pressurized air from pressurized air line 65 exits through sample probe 14 to dislodge any particulates clogging the sample probe filter.

Figure 4:
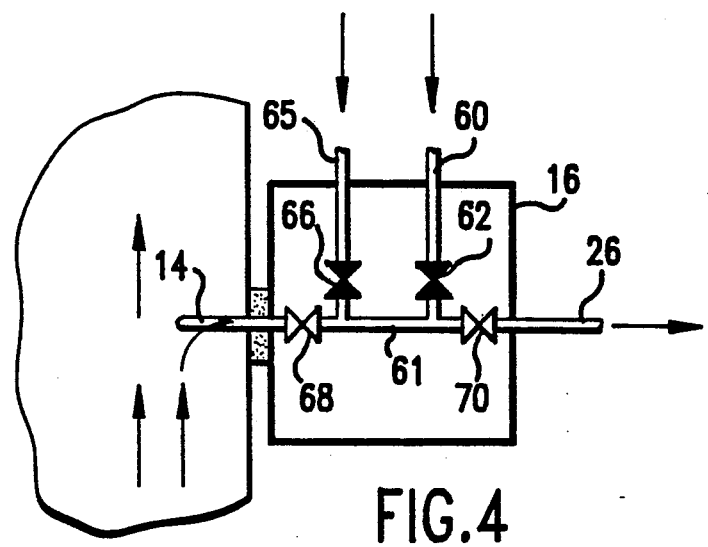
FIG. 4 an enlarged view of the valve box and gas sampling probe of another embodiment of a gas sampling and analyzing system of the present invention.

An alternative embodiment of valve box 16 is shown in FIG. 4. In this embodiment, the single valve 64 is replaced by an upstream sample line valve 68 and a downstream sample line valve 70. With the valve arrangement shown in FIG. 4, valves 68 and 70 are opened while valves 66 and 62 are closed when it is desired to analyze a gas sample from flue stack 12. Alternatively, valves 62 and 70 are opened while valves 66 and 68 are closed when it is desired to analyze a known calibration gas. Alternatively, valves 66 and 68 are opened while valves 62 and 70 are closed when it is desired to pump pressurized air out of sample probe 14 to clean the sample probe filter. Other alternative valve arrangements may be utilized in valve box 16 to obtain similar sample taking control.

It will be apparent to those skilled in the art that modifications and variations can be made in the gas sampling and analyzing system of this invention. The invention in its broader aspects is, therefore, not limited to the specific details, representative apparatus, and illustrative examples shown and described above. Thus, it is intended that all matter contained in the foregoing description or shown in the accompanying drawings shall be interpreted as illustrative and not in a limiting sense.

What is claimed is:

1. A system for sampling a gas stream and for analyzing the gas stream sample, comprising:

means for taking a gas sample from the gas stream;

means for conditioning the gas sample, said conditioning means receiving the gas sample and removing moisture therefrom and being disposed proximate to said sampling means, means for analyzing the gas sample to determine the concentration of at least one component of the gas sample, said analyzing means being at a location distant from said sampling means and said conditioning means;

a first gas sample transport line fluidically connecting said conditioning means to said analyzing means to conduct the gas sample from said conditioning means to said analyzing means; and a second gas sample transport line fluidically connecting said sampling means to said conditioning means to conduct the gas sample from said sampling means to said conditioning means, said conditioning means including:

a first condenser;

a first drain to remove condensed liquid from said first condenser;

a gas sample pump having an inlet and an outlet, said gas sample pump creating a gas suction at its inlet and a gas exhaust pressure at its outlet, said pump inlet being in fluidic communication with said first condenser to draw the gas sample through said sampling means and said first condenser into said sample pump inlet, said sample pump outlet being in fluidic communication with said first gas sample transport line;

a second condenser in which vapor in the gas sample is condensed, said second condenser being in fluidic communication with said sample pump outlet and said first transport line such that the gas sample discharged from said pump outlet enters said second condenser before entering said first sample transport line, the pressure of the sample in said second condenser being greater than ambient air pressure outside said system; and a second drain to remove condensed liquid from said second condenser;

said first and second condensers including refrigerated coils through which the gas sample passes.

* * * * *